(12) United States Patent
Wray et al.

(10) Patent No.: US 8,580,772 B2
(45) Date of Patent: Nov. 12, 2013

(54) COMBINATION THERAPIES USING MELENGESTROL ACETATE AND ZILPATEROL OR ITS SALTS

(75) Inventors: Mary Irene Wray, Desoto, KS (US); Damon Edward Bradley, Desoto, KS (US); Melissa A. Petersen, Desoto, KS (US); Auddie Sharp, Desoto, KS (US); Celia Shelton, Lewes, DE (US); Jayden Lloyd Montgomery, Winston-Salem, NC (US)

(73) Assignee: Intervet Inc., Summit, NJ (US)

( * ) Notice: Subject to any disclaimer, the term of this patent is extended or adjusted under 35 U.S.C. 154(b) by 512 days.

(21) Appl. No.: 12/327,885

(22) Filed: Dec. 4, 2008

(65) Prior Publication Data

US 2009/0181906 A1  Jul. 16, 2009

Related U.S. Application Data

(60) Provisional application No. 60/992,922, filed on Dec. 6, 2007.

(51) Int. Cl.
- *A61K 31/56* (2006.01)
- *A61K 31/35* (2006.01)
- *A61K 31/34* (2006.01)
- *A01N 43/00* (2006.01)

(52) U.S. Cl.
USPC ............ 514/171; 514/211.12; 514/211.15; 514/453; 514/461

(58) Field of Classification Search
USPC ............ 514/171, 211.12, 211.15, 453, 461
See application file for complete search history.

(56) References Cited

U.S. PATENT DOCUMENTS

| | | | |
|---|---|---|---|
| 3,359,287 A | 12/1967 | Babcock et al. | |
| 3,417,182 A | 12/1968 | Babcock et al. | |
| 4,154,748 A | 5/1979 | Van Rheenen et al. | |
| 4,585,770 A | 4/1986 | Frechet et al. | |
| 4,900,735 A | 2/1990 | Grandadam | |
| 5,731,028 A | 3/1998 | Chevremont et al. | |
| 5,847,124 A | 12/1998 | Chevremont et al. | |
| 6,498,153 B1 | 12/2002 | Cady et al. | |
| 7,207,289 B2 | 4/2007 | Montgomery | |

FOREIGN PATENT DOCUMENTS

WO  WO 2008006828  *  1/2008

OTHER PUBLICATIONS

Elam et al., "Effect of zilpaterol hydrochloride duration of feeding on performance and carcass characteristics of feedlot cattle", Journal of Animal Science, 2009, pp. 2133-2141, vol. 87.

Etherton et al., "Somatotropin and β-adrenergic agonists: Their efficacy and mechanisms of action", Journal of Animal Science, 1991, pp. 2-26, vol. 69.

Goodrich et al., "Influence of Monensin on the Performance of Cattle", Journal of Animal Science, 1984, pp. 1484-1498, vol. 58.

Laudert et al., "Tylan Efficacy—A 40-trial Summary", Elanco Tech Talk, 1994, AI11115.

Mersmann, H. J., "Overview of the effects of beta-adrenergic receptor agonists on animal growth including mechanisms of action", Journal of Animal Science, 1998, pp. 160-172, vol. 76.

Montgomery et al., "Effects of dietary zilpaterol hydrochloride on feedlot performance and carcass characteristics of beef steers fed with and without monensin and tylosin", Journal of Animal Science, 2009, pp. 1013-1023, vol. 87.

Montgomery et al., "Dietary zilpaterol hydrochloride. I. Feedlot performance and carcass traits of steers and heifers", Journal of Animal Science, 2009, pp. 1374-1383, vol. 87.

Nagaraja et al., Liver abscesses in feedlot cattle: a review., Journal of Animal Science, 1998, pp. 287-298, vol. 76.

Perrett et al., "Evaluation of the Efficacy and Cost-Effectiveness of Melengestrol Acetate in Feedlot Heifer Valves in Western Canada", Veterinary Therapeutics, 2008, pp. 223-240, vol. 9, No. 3.

Potter et al., "Effect of Monensin and tylosin on Average Daily Gain, Feed Efficiency and Liver Abscess Incidence in Feedlot Cattle", Journal of Animal Science, 1985, pp. 1058-1065, vol. 61.

Raun et al., "Effect of Monensin on Feed Efficiency of Feedlot Cattle", Journal of Animal Science, 1976, pp. 670-677, vol. 43.

Richardson et al., "Effect of Monensin on Rumen Fermentation in Vitro and in Vivo", Journal of Animal Science, 1976, pp. 657-664, vol. 43.

Sides et al., "Effect of Feeding Melengestrol Acetate, Monensin, and Tylosin on Performance, Carcass Measurements, and Liver Abscesses of Feedlot Heifers", The Professional Animal Scientist, 2009, pp. 459-464, vol. 25.

Avendano-Reyes et al., "Effects of two β-adrenergic agonists on finishing performance, carcass characteristics, and meat quality of feedlot steers", Journal of Animal Science, 2006, pp. 3259-3265, vol. 84(12).

Henricks et al., "Serum Concentrations of Trenbolone-17β and Estradiol-17β and Performance of Heifers Treated With Trenbolone Acetate, Melengestrol Acetate, or Estradiol-17β", Journal of Animal Science, 1997, pp. 2627-2633, vol. 75(10).

Schiffer et al., The Fate of Trenbolone Acetate and Melengestrol Acetate after Application as Growth Promoters in Cattle: Environmental Studies, Environmental Health Perspectives, 2001, pp. 1145-1151, vol. 109(11).

* cited by examiner

*Primary Examiner* — Renee Claytor

(57) ABSTRACT

This invention generally relates to a method for promoting growth and increasing feed utilization efficiency in animals, and, more specifically, to combinations comprising zilpaterol (and salts thereof) and melengestrol acetate. Included within this invention are treatment methods comprising the administration of such combinations to animals, compositions comprising such combinations, uses of such combinations to prepare medicaments, and kits for using such combinations.

21 Claims, No Drawings

COMBINATION THERAPIES USING MELENGESTROL ACETATE AND ZILPATEROL OR ITS SALTS

PRIORITY CLAIM TO RELATED PATENT APPLICATIONS

This patent claims priority to 60/992,922 (filed Dec. 6, 2007). The entire text of each of the above-referenced patent applications is hereby incorporated by referenced into this patent.

FIELD OF THE INVENTION

This invention generally relates to a method for promoting growth and increasing feed utilization efficiency in animals, and, more specifically, to combinations comprising zilpaterol (and salts thereof) and melengestrol acetate. Included within this invention are treatment methods comprising the administration of such combinations to animals, compositions comprising such combinations, uses of such combinations to prepare medicaments, and kits for using such combinations.

BACKGROUND OF THE INVENTION

In many countries, commercial livestock rearing systems have become commonplace. Commercial animal husbandry techniques have been used to rear, for example, livestock, poultry, and fish. These techniques have resulted in greatly increased production of food products from such animals. Successful commercial raising of animals, particularly for food, requires maximization of the growth rate and feed utilization efficiency to reduce the unit cost of production. This has led to the development and widespread use of feed additives.

Zilpaterol is a known adrenergic β-2 agonist corresponding in structure to Formula (I):

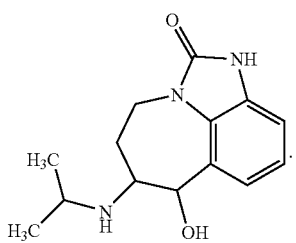

The IUPAC name for zilpaterol is 4,5,6,7-tetrahydro-7-hydroxy-6-(isopropylamino) imidazo[4,5,1-jk]-[1]benzazepin-2(1H)-one. The Chemical Abstracts name for zilpaterol is 4,5,6,7-tetrahydro-7-hydroxy-6-[(1-methyl-ethyl)amino]-imidazo[4,5,1-jk][1]benzazepin-2(1H)-one.

Zilpaterol hydrochloride is sold by Intervet Inc., a part of Schering-Plough Corporation, under the trademark ZILMAX®. It is approved in the United States for cattle fed in confinement for harvest at daily doses ranging from 60 to 90 mg/animal to increase the rate of weight gain, improve feed efficiency, and increase carcass leanness during the last 20 to 40 days on feed. See NADA No. 141-258.

In U.S. Pat. No. 4,585,770, Fréchet et al. discuss compounds, such as zilpaterol, encompassed by a genus characterized as 6-amino-7-hydroxy-4,5,6,7-tetrahydro-imidazo[4,5,1-j-k][1]-benzazepin-2-(1H)-one derivatives and acid addition salts thereof. Fréchet et al. state that such compounds may be used as an active ingredient for inducing antihypertensive and hypotensive activity in a warm-blooded animal.

In U.S. Pat. No. 4,900,735, Grandadam discusses a zootechnical composition comprising zilpaterol and acid addition salts thereof. Grandadam states that such a composition may be used to increase the weight of cattle, pigs, sheep, and poultry. Grandadam also discusses combination therapies that further comprise the administration of a steroid corresponding in structure to Formula (II):

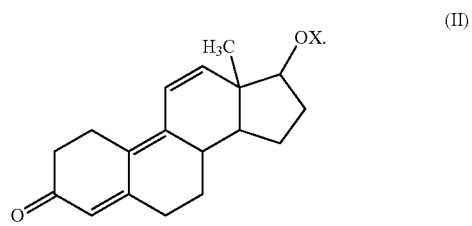

Here, X is selected from the group consisting of hydrogen, optionally unsaturated alkyl of 1 to 6 carbon atoms wherein one of the carbon atoms may be replaced by oxygen, and acyl of an organic carboxylic acid of 1 to 18 carbon atoms. Such compounds include trenbolone acetate, wherein X is —C(O)CH₃. Trenbolone acetate is approved in the United States for use, alone and in combination with other active ingredients, in various implants in cattle to increase the rate of weight gain and improve feed efficiency. See NADA Nos. 138-612, 140-897, 140-992, 414-043, 141-269, 200-221, 200-224, 200-346, and 200-367. Grandadam goes onto discuss combinations that further comprise the administration of zeranol or estradiol (i.e., 17β-estra-1,3,5(10)-triene-3,17-diol). Zeranol is approved in the United States for use in implants to increase the rate of weight gain and improve feed efficiency in cattle and sheep. See NADA Nos. 038-233 and 141-0192. Estradiol and estradiol benzoate are approved in the United States for use in combination with other active ingredients in various implants for increasing the rate of weight gain and improving feed efficiency in cattle. See NADA Nos. 009-576, 011-427, 110-315, 118-123, 135-906, 140-897, 140-992, 141-043, 141-269, 200-221, 200-346, and 200-367.

In U.S. Pat. Nos. 5,731,028 and 5,847,124, Chevremont et al. discuss crystallized anhydrous zilpaterol hydrochloride, and particularly crystallized anhydrous zilpaterol hydrochloride wherein less than 5% of the crystals have a size of less than 15 μm, and at least 95% of the crystals have a size of less than 250 μm. According to Chevremont et al., such crystals may be incorporated into animal feed to increase body weight and meat quality. Chevremont et al. provide methods for making such crystals, and discuss using the crystals to make animal premixes in which the crystals are secured to a corn cob support having a greater particle size. They also discuss monohydrate and trihydrate intermediates that can be useful in, for example, making the crystals.

In U.S. Pat. No. 7,207,289, Montgomery discusses methods for increasing beef production, reducing feed intake while maintaining beef production, and reducing incidences of liver abscess in cattle. These methods comprise administering a feed comprising an ionophore and macrolide antibiotic during an initial period, and then administering a feed comprising zilpaterol (including zilpaterol hydrochloride) with essentially no ionophore or macrolide antibiotic Melengestrol acetate (or "17α-acetoxy-6-methyl-16-methylenepregna-4,6-diene-3,20-dione") corresponds in structure to Formula (III):

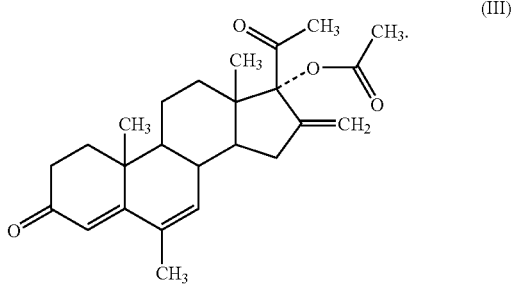 [SMILES: C=C1CC2C3C=C(C)C4=CC(=O)CCC4(C)C3CCC2(C)[C@@]1(OC(C)=O)C(C)=O]

It is reported to be an orally-active progestogen that inhibits estrus and ovulation, and increases weight gain in heifers. It is commercially available from Pfizer Animal Health under the trade name MGA®. U.S. Pat. No. 3,359,287 discusses preparation of melengestrol acetate by dehydrogenating 17α-hydroxy-6α-methyl-16-methylenepregn-4-ene-3,20-dione 17-acetate with chloranil. U.S. Pat. No. 4,154,748 discusses an alternative process wherein melengestrol acetate is prepared by a process comprising acetylation of 17α-hydroxy-6-methyl-16-methylenepregna-4,6-diene-3,20-dione.

Melengestrol acetate is approved in the United States for feeding to heifers for harvest at doses ranging from 0.25 to 0.50 mg/heifer daily to increase weight gain, improve gain efficiency, and suppress estrus. See NADA 034-254, 039-402, and 200-343. It is generally fed to heifers for 90 to 150 days before harvest. It also has been approved in the United States for the following combinations:
  a) With oxytetracycline to increase the rate of weight gain, improve feed efficiency, suppress estrus, and reduce liver condemnation due to liver abscesses. See NADA 046-718 and 046-719
  b) With monensin sodium to increase the rate of weight gain, improve feed efficiency, suppress estrus, and prevent and control coccidiosis due to *Eimeria bovis* and *Eimeria zuernii*. See NADA 124-309, 125-476, and 200-422.
  c) With tylosin phosphate to increase the rate of weight gain, improve feed efficiency, suppress estrus, and reduce incidence of liver abscesses. See NADA 138-995, 139-192, and 200-427.
  d) With lasalocid to increase the rate of weight gain, improve feed efficiency, and suppress estrus. See NADA 139-876, 140-288, and 200-451.
  e) With monensin sodium and tylosin phosphate to increase the rate of weight gain, improve feed efficiency, suppress estrus, prevent and control coccidiosis due to *Eimeria bovis* and *Eimeria zuernii*, and reduce incidence of liver abscesses caused by *Fusobacterium necrophorum* and *Actinomyces* (*Corynebacterium*) *pyogenes*. See NADA 138-792, 138-870, and 200-375.
  f) With tylosin phosphate and lasalocid to increase the rate of weight gain, improve feed efficiency, suppress estrus, and reduce incidence of liver abscesses. See NADA 138-904, 138-992, and 200-430.
  g) With monensin sodium and ractopamine hydrochloride to increase the rate of weight gain, improve feed efficiency, suppress estrus, increase carcass leanness, and prevent and control coccidiosis due to *Eimeria bovis* and *Eimeria zuernii*. See NADA 141-234 and 200-448.
  h) With monensin sodium, tylosin phosphate, and ractopamine hydrochloride to increase the rate of weight gain, improve feed efficiency, suppress estrus, increase carcass leanness, prevent and control coccidiosis due to *Eimeria bovis* and *Eimeria zuernii*, and reduce liver abscesses caused by *Fusobacterium necrophorum* and *Actinomyces* (*Corynebacterium*) *pyogenes*. See NADA 141-233 and 200-424.

U.S. Pat. No. 3,417,182 discusses using melengestrol acetate to control estrual periods and stimulate growth of domestic birds and other animals.

There still exists a need for alternative methods and compositions for increasing the rate of weight gain and improving feed efficiency in animals, particularly animals raised for food, such as livestock, poultry, and/or fish. The following disclosure describes such methods and compositions.

SUMMARY OF THE INVENTION

Briefly, this invention is directed, in part, to a method for improving feed utilization efficiency and/or increasing the rate of weight gain in an animal, particularly an un-spayed female animal. The animal may be, for example, a livestock animal (e.g., a bovine, sheep, goat, or other ruminant; swine; etc.), bird (e.g., a chicken, turkey, etc.), or fish (e.g., a salmon, trout, catfish, etc.). The method comprises administering to the animal zilpaterol (or a salt thereof, such as zilpaterol hydrochloride) and melengestrol acetate. Other benefits of this method generally include, for example, increases in carcass leanness.

This invention also directed, in part, to uses of zilpaterol (or a salt thereof) and melengestrol acetate to make a medicament. Such a medicament is generally useful for improving feed utilization efficiency or increasing the rate of weight gain in an animal. Other uses of such a medicament generally include, for example, increasing carcass leanness.

This invention also is directed, in part, to a composition. The composition comprises zilpaterol (or a salt thereof) and melengestrol acetate.

This invention also is directed, in part, to an animal feedstuff for improving the efficiency of feed utilization or increasing the rate of weight gain in an animal. The feedstuff comprises a composition, which, in turn, comprises zilpaterol (or a salt thereof) and melengestrol acetate. The feedstuff also comprises at least one carrier material.

This invention also is directed, in part, to kits for administering zilpaterol (or a salt thereof and melengestrol acetate to an animal.

In some embodiments directed to kits, the kit comprises a zilpaterol dosage form comprising zilpaterol (or a salt thereof). In some such embodiments, the kit also comprises at least one of the following: (a) a melengestrol acetate dosage form comprising melengestrol acetate, (b) instructions for administering zilpaterol (or a salt thereof) and melengestrol acetate to the animal, and (c) instructions for mixing at least a portion of the zilpaterol dosage form with melengestrol acetate.

In some embodiments directed to kits, the kit comprises a melengestrol acetate dosage form comprising melengestrol acetate. In some such embodiments, the kit also comprises at least one of the following: (a) a zilpaterol dosage form comprising zilpaterol (or a salt thereof), (b) instructions for administering melengestrol acetate and zilpaterol (or a salt thereof) to the animal, and (c) instructions for mixing at least a portion of the melengestrol acetate dosage form with zilpaterol (or a salt thereof).

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

It has been discovered that the combination of zilpaterol (or a salt thereof, such as zilpaterol hydrochloride) and melengestrol acetate can be particularly useful for increasing the rate of weight gain and improving feed efficiency (i.e., decrease the amount of feed per amount of weight gain) in animals. Other uses include, for example, increasing carcass leanness (i.e., increasing protein content in carcass soft tissue).

A salt of zilpaterol may be advantageous in the combination due to one or more of the salt's physical properties, such as pharmaceutical stability in differing temperatures and humidities; crystalline properties; and/or a desirable solubility in water, oil, or other solvent. Any such salt preferably is pharmaceutically acceptable. Suitable zilpaterol salts generally include acid addition salts. An acid addition salt typically can be prepared by reacting free zilpaterol base with an approximately stoichiometric amount of an inorganic or organic acid. Examples of often suitable inorganic acids include hydrochloric, hydrobromic, hydroiodic, nitric, carbonic, sulfuric, and phosphoric acid. Examples of often suitable organic acids generally include, for example, aliphatic, cycloaliphatic, aromatic, araliphatic, heterocyclic, carboxylic, and sulfonic classes of organic acids. Specific examples of often suitable organic acids include cholate, sorbate, laurate, acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, aryl carboxylic acid (e.g., benzoate), anthranilic acid, mesylate, stearate, salicylate, p-hydroxybenzoate, phenylacetate, mandelate, embonate (pamoate), alkylsulfonate (e.g., ethanesulfonate), arylsulfonate (e.g., benzenesulfonate), pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate. In some embodiments, the salt of zilpaterol comprises a hydrochloric acid salt.

Included within the scope of the compounds and salts used in the combinations of this invention are any stereoisomers, tautomers, and mixtures thereof.

The combination of this invention may generally be used, for example, to increase the rate of weight gain, improve feed efficiency, and/or increase carcass leanness in animals raised for food. These include, for example, livestock (e.g., bovine and other ruminant animals, swine animals, etc.), poultry (e.g., chickens, turkeys, etc.), and/or fish (e.g., salmon, trout, catfish, etc.). The dosing regimen of the zilpaterol (or salt thereof) and melengestrol acetate is preferably chosen to maximize one or more beneficial effects of the combination.

In some embodiments, the combination of this invention is orally administered. Suitable oral dosage forms may include, for example, solid dosage forms (e.g., tablets, hard or soft capsules, granules, powders, etc.), pastes, and liquid dosage forms (e.g., solutions, suspensions, syrups, etc.).

In some embodiments, at least one of the zilpaterol (or salt thereof) and melengestrol acetate is incorporated into the intended recipient animal's drinking water.

In some embodiments, at least one (and often both) of the zilpaterol (or salt thereof) and melengestrol acetate is incorporated into the intended recipient animal's feed. The zilpaterol (or salt thereof) and/or melengestrol acetate may be mixed with the feed directly or as part of a premix. Incorporating both the zilpaterol (or salt thereof) and melengestrol acetate into the feed is often particularly preferable for cattle or swine in a feedlot.

In some embodiments, the zilpaterol (or salt thereof) and melengestrol acetate are mixed together or separately with one or more carrier materials. A suitable carrier material may be, for example, a normal daily feed. Alternative (or additional) carrier materials may include one or more excipients such as, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), lubricating agents (e.g., magnesium stearate, stearic acid, or talc), wetting or dispersing agents, etc. Liquid compositions will generally comprise at least one solvent. The solvent(s) typically has sufficient chemical properties and is in a sufficient quantity to keep the zilpaterol (or salt thereof) and/or melengestrol acetate solubilized at normal storage and usage temperatures. In some instances, a liquid composition will comprise at least one preservative. The presence of a preservative may, for example, allow for the composition to be stored over a greater amount of time.

In some embodiments, the zilpaterol (or salt thereof) and/or melengestrol acetate is in the form of particles adhered to a support, which, in turn, is fed to the intended recipient animal by, for example, being introduced into the intended recipient animal's feed, either directly or as part of a premix. Contemplated supports include, for example, inert supports, such as calcium carbonate, limestone, oyster shell flour, talc, soybean hulls, soybean meal, soybean feed, soybean mill run, wheat middling, rice hulls, corn meal, corn germ meal, corn gluten, starch, sucrose, and lactose. Particularly contemplated supports include corn cob supports, such as the support discussed in U.S. Pat. No. 5,731,028.

In some embodiments in which one or more of the active ingredients are supported, the active ingredient particles adhered to the support have a particle size that is less than the size of the support. In some embodiments employing a corn cob support, for example, the size of the support is from about 300 to about 800 μm. In some such embodiments, the active ingredient particles (or at least about 95% of the active agent particles) are less than about 250 μm. In some such embodiments, the size of the majority of the active ingredient particles is from about 50 to about 200 μm. To avoid generating dust when making the supported composition, it is generally preferable to avoid using extremely small active ingredient particles. In some embodiments, for example, size distribution of the active ingredient particles is such that less than about 5% of the particles have a particle size of less than about 15 μm.

To the extent the combination is incorporated into feed, the feed mixture will vary depending on, for example, the type (e.g., species and breed), age, weight, activity, and condition of the intended recipient. With bovine and swine animals, for example, various feeds are well known in the art, and often comprise cereals; sugars; grains; arachidic, tournsole, and soybean press cake; flours of animal origin, such as fish flour;

amino acids; mineral salts; vitamins; antioxidants; etc. In general, the zilpaterol (or salt thereof) and melengestrol acetate can be incorporated into any feed that is available and used for the intended recipient animal.

It is contemplated that the zilpaterol (or salt thereof) and/or melengestrol acetate may be administered via non-oral routes, such as rectally, via inhalation (e.g., via a mist or aerosol), transdermally (e.g., via a transdermal patch), or parenterally (e.g., subcutaneous injection, intravenous injection, intramuscular injection, implanted device, partially implanted device etc.). It is contemplated, for example, that at least one of the zilpaterol (or salt thereof) and melengestrol acetate may be administered via an implant, such as a subcutaneous implant. For administration to bovine or swine animals, for example, the zilpaterol (or salt thereof) and/or melengestrol acetate may be administered in the form of an implant behind the ear. If the zilpaterol (or salt thereof) and/or the melengestrol acetate is/are administered parenterally via an injection, the concentration of the active agent(s) in the dosage form preferably is sufficient to provide the desired amount of the active agent(s) in a volume that is acceptable for parenteral administration.

Factors affecting the preferred dosage regimen may include, for example, the type (e.g., species and breed), age, size, diet, activity, and condition of the intended recipient; the type of administration used (e.g., oral via feed, oral via drinking water, subcutaneous implant, other parenteral route, etc.); pharmacological considerations, such as the activity, efficacy, pharmacokinetic, and toxicology profiles of the particular composition administered; and whether the zilpaterol (or its salt) and melengestrol acetate are being administered as part of a combination with additional active ingredients. Thus, the preferred amounts of the zilpaterol (or salt thereof) and melengestrol acetate can vary, and, therefore, can deviate from the typical dosages set forth above.

It is contemplated that one or both of the zilpaterol (or salt thereof) and melengestrol acetate may be administered once. In general, however, the combination is administered over time, and the period of time over which the zilpaterol (or salt thereof) is administered overlaps (at least partially) with the period of time over which the melengestrol acetate is administered. In some embodiments, the zilpaterol (or salt thereof) and melengestrol acetate are co-administered daily over a period of time in a substantially simultaneous manner, such as, for example, (a) in a single formulation (e.g., in the same tablet, granule, or powder) having a fixed ratio(s) of the zilpaterol (or salt thereof) to the melengestrol acetate, and/or (b) in separate formulations. The zilpaterol (or salt thereof) and melengestrol acetate may alternatively (or additionally) be administered at different intervals over a period of time.

In some embodiments (e.g., where the animal recipient is a livestock animal), the zilpaterol (or a salt thereof) is administered approximately daily for at least about 2 days, more typically daily for from about 10 to about 60 days, and still more typically, from about 14 to about 42 days. In some embodiments (e.g., where the animal is a bovine animal), the zilpaterol (or a salt thereof) is administered approximately daily for from about 20 to about 40 days. In some such embodiments, for example, the composition is administered approximately daily for from about the last 20 to about the last 40 days of the finishing period. The term "finishing period" refers to the later stage of the growing period for an animal. During this period, the recipient animal is typically confined (e.g., in a feedlot for livestock animals). In some embodiments where the animal is a bovine animal, this period lasts for from about 90 to about 225 days, and depends on, for example, the starting body weight of the animal. There is typically a withdrawal period following the finishing period in which no zilpaterol (or salt thereof) is administered. The length of this withdrawal period may depend on, for example, the type (e.g., species and breed), age, weight, activity, and condition of the recipient animal, as well as the maximum acceptable residue concentration in the meat of the animal.

In general, the melengestrol acetate is administered to the intended animal recipient daily during at least a portion of the period (and typically the entire period) that the zilpaterol (or a salt thereof) is administered. The melengestrol acetate also is typically administered for a period before the zilpaterol (or zilpaterol salt) is administered, and, in some instances, for at least a portion of the zilpaterol (or zilpaterol salt) withdrawal period afterward. In some embodiments, for example, the melengestrol acetate is administered approximately daily during the entire time that the animal is being fed in confinement for harvest, including before, during, and after the time that the zilpaterol (or salt thereof) is administered.

Although single daily doses are typically preferred, it is contemplated that shorter or longer periods between doses can be used, depending on, for example, the recipient's metabolism of the zilpaterol (or its salt) and the melengestrol acetate. It is contemplated that smaller doses may be administered two or more times per day to achieve the desired total daily dose. Such multiple doses per day may, in some instances, be used to increase the total oral daily dose, if desired.

In accordance with this invention, the zilpaterol (or salt thereof) and melengestrol acetate are generally used in amounts that, when combined, produce an unexpected benefit. It is believed, for example, that this combination provides an unexpected benefit with respect to improvement of feed utilization efficiency and/or increasing the rate of weight gain. Other benefits include, for example, increases in carcass leanness.

In some embodiments, the amount of the zilpaterol (or salt thereof) and the amount of melengestrol acetate are, when combined, sufficient to improve the animal's average daily feed utilization efficiency over a period of at least about 3 days (or at least about 7 days, at least about 10 days, at least about 20 days, at least about 30 days, or at least about 40 days) relative to the average daily feed utilization efficiency that would be realized by administering the amount of the zilpaterol (or salt thereof) without any melengestrol acetate over the same amount of time under otherwise substantially identical feeding conditions.

In some embodiments, the amount of the zilpaterol (or salt thereof) and the amount of melengestrol acetate are, when combined, sufficient to increase the animal's average daily weight gain over a period of at least about 3 days (or at least about 7 days, at least about 10 days, at least about 20 days, at least about 30 days, or at least about 40 days) by at least about 100% (or at least about 125%, at least about 150%, at least about 175%, or at least about 200%) the average daily weight gain that is realized during the week immediately before administration of the zilpaterol (or salt thereof) and melengestrol acetate under otherwise substantially identical feeding conditions.

In some embodiments, the amount of the zilpaterol (or salt thereof and the amount of melengestrol acetate are, when combined, sufficient to increase the animal's average daily weight gain over a period of at least about 3 days (or at least about 7 days, at least about 10 days, at least about 20 days, at least about 30 days, or at least about 40 days) relative to the average daily weight gain that would be realized by administering the amount of the zilpaterol (or salt thereof) without any melengestrol acetate over the same amount of time under otherwise substantially identical feeding conditions. In some such embodiments, for example, the amount of the zilpaterol (or salt thereof) and the amount of melengestrol acetate are, when combined, sufficient to increase the animal's average daily weight gain over a period of at least about 3 days (or at least about 7 days, at least about 10 days, at least about 20 days, at least about 30 days, or at least about 40 days) by at least about 1.2 times (or at least about 1.5 times, at least about 1.7 times, at least about 2.0 times, or at least about 2.1 times) the average daily weight gain that would be realized by administering the amount of the zilpaterol (or salt thereof) without any melengestrol acetate over the same amount of time under otherwise substantially identical feeding conditions.

The total daily dose of the zilpaterol (or a salt thereof) is typically a least about 1 mg/animal, particularly in the context of, for example, livestock. In some embodiments, for example, the daily dose is less than about 900 mg/animal. In some such embodiments, the daily dose is from about 1 to about 200 mg/animal, from about 20 to about 150 mg/animal, from about 50 to about 100 mg/animal, or from about 60 to about 90 mg/animal. In some embodiments, greater than about 0.01 mg/kg (i.e., milligram of zilpaterol (or salt thereof) per kilogram body weight) is fed daily during the treatment period, particularly for bovine and swine animals. In some such embodiments, the daily dose is from about 0.01 to about 15 mg/kg, from about 0.01 to about 10 mg/kg, from about 0.05 to about 2 mg/kg, from about 0.1 to about 1, or from about 0.1 to about 0.3 mg/kg. To illustrate, in some embodiments for heifers, the daily dose is from about 0.1 to about 0.2 mg/kg (e.g., about 0.15 mg/kg daily). Illustrating further, in some embodiments for swine animals, the total daily dose is from about 0.13 to about 0.27 mg/kg.

In some embodiments where the zilpaterol (or salt thereof) is administered in the recipient animal's feed, the concentration of the zilpaterol (or salt thereof) in the feed is at least about 0.01 ppm (by weight). In some embodiments for bovine animals, the concentration of zilpaterol (or a salt thereof) is no greater than about 75 ppm (by weight). In some such embodiments, for example, the concentration of zilpaterol (or its salt) is no greater than about 38 ppm. In other embodiments, the concentration (or its salt) is from about 0.5 to about 20 ppm, from about 3 to about 8 ppm, or from about 3.7 to about 7.5 ppm (by weight). In some embodiments for swine animals, the concentration of zilpaterol (or a salt thereof) is no greater than about 45 ppm (by weight). In some such embodiments, for example, the concentration is no greater than about 23 ppm. In other embodiments, the concentration of zilpaterol (or its salt) is from about 0.5 to about 20 ppm, from about 2 to about 10 ppm, or from about 4 to about 8 ppm (by weight). The zilpaterol and zilpaterol salt concentrations in this paragraph are all based on a feed containing approximately 90% dry matter.

In general, the total daily dose of melengestrol acetate is at least about 0.001 mg/animal, particularly in the context of, for example, livestock. In some such embodiments, for example, the daily dose is less than about 5 mg/animal. To illustrate, in some embodiments, the daily dose is from about 0.01 to about 2 mg/animal, from about 0.05 to about 1 mg/animal, from about 0.1 to about 1 mg/animal, from about 0.25 to about 0.5 mg/animal, or from about 0.25 to about 0.4 mg/animal. In some embodiments, the daily dose is greater than about 0.0001 mg/kg (i.e., milligram of melengestrol acetate per kilogram body weight). In some embodiments directed to bovine animals, the daily dose is from about 0.0005 mg/kg to about 0.001 mg/kg. In some embodiments directed to swine animals, the daily dose is from about 0.001 to about 0.008 mg/kg.

In some embodiments where the melengestrol acetate is administered in the recipient animal's feed, the concentration of the melengestrol acetate in the feed is at least about 0.001 ppm (by weight). In some embodiments, the melengestrol acetate concentration is from about 0.002 to about 0.6 ppm, from about 0.002 to about 0.3 ppm, from about 0.002 to about 1 ppm, from about 0.002 to about 0.6 ppm, or from about 0.01 to about 0.1 ppm (by weight). In some such embodiments, melengestrol acetate is administered in the feed at a concentration of from about 0.02 to about 0.06 ppm (by weight). The melengestrol acetate concentrations in this paragraph are all based on a feed containing approximately 90% dry matter.

In some embodiments, the zilpaterol (or salt thereof) and melengestrol acetate are administered at a mass ratio of the zilpaterol (or salt thereof) to melengestrol acetate of from about 10 to about 1000, from about 50 to about 500, from about 100 to about 400, from about 120 to about 360, or from about 130 to about 170. In some embodiments, this mass ratio preferably is maintained approximately daily for at least about 2 days, and typically from about 10 to about 60 days, or from about 14 to about 42 days. In some embodiments (e.g., where the animal is a bovine animal), the mass ratio is maintained approximately daily for from about 20 to about 40 days. In some such embodiments, for example, the mass ratio is maintained approximately daily for from about the last 20 to about the last 40 days of the finishing period. In some embodiments, this mass ratio is present in a composition (e.g., feed) that is administered daily to the recipient animal.

In some embodiments, the combination of this invention is administered in combination with one or more further active ingredients. It is contemplated that the additional active ingredient(s) may be administered once. In general, however, the additional active ingredient(s) is administered over time. In such instances, the additional active ingredient(s) may be administered substantially simultaneously with one or both of the zilpaterol (or salt thereof) and melengestrol acetate and/or at different intervals. To the extent the administration is simultaneous, the combined actives may be part of the same dosage formulation (e.g., in the same tablet, granule, or powder) and/or separate formulations.

In some embodiments (e.g., for livestock, such as bovine or swine), the combination of this invention is administered with one or more steroids in addition to the melengestrol acetate.

In some embodiments, the combination of this invention is administered as part of a dosing scheme with a steroid corresponding in structure to Formula (IV):

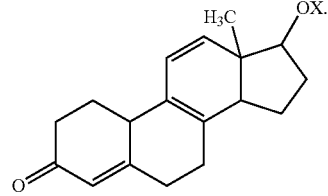

(IV)

In Formula (IV), X may be, for example, hydrogen; optionally unsaturated alkyl of from 1 to about 6 carbon atoms, wherein one of the carbon atoms optionally is replaced by —O—; or an acyl of an organic carboxylic acid of from 1 to about 18 carbon atoms. In some such embodiments, for example, X is —C(O)CH$_3$ (i.e., the steroid comprises trenbolone acetate, also known as "17β-acetoxy-Δ$^{4,9,11}$-estratriene-3-one"). That compound corresponds in structure to Formula (V):

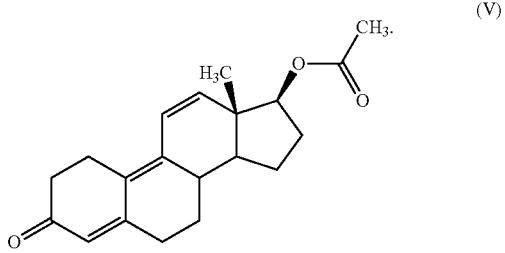 [SMILES: CC(=O)O[C@H]1CCC2C3CCC4=CC(=O)CCC4=C3C=C[C@@]21C]

Trenbolone acetate is marketed by Intervet Inc., a part of Schering-Plough Corporation, under the trademarks Finaplix® and Revalor®. For livestock in particular, trenbolone acetate may generally be administered parenterally, such as via injection or a subcutaneous implant. The implant may be in the form of a single or, more typically, multiple units (e.g., pellets). Suitable locations for a subcutaneous implant generally include, for example, behind the ear. In some embodiments, the implant is implanted for from about 20 days to about 8 months before harvest, or from about 2 to about 7 months before harvest. The total trenbolone acetate implant dosage is typically less than about 4000 mg/animal. In some embodiments, the total trenbolone acetate implant dosage is from about 50 to about 2000 mg/animal, or from about 80 to about 500 mg/animal. In some embodiments, the preferred daily trenbolone acetate dosage is from about 0.75 to about 1.2 mg/animal (e.g., about 0.95 mg/animal daily). In some embodiments, implants are implanted sequentially to administer the desirable amount of trenbolone acetate over time. In some embodiments, immediate- and delayed-release implant units (e.g., pellets) are implanted at the same time to administer a desirable amount of trenbolone acetate over time. The timing of the initial implant and any subsequent implants, as well as the amount of trenbolone acetate in the implant, will depend, for example, the species of the recipient animal, the size of the recipient animal, and the formulation(s) of the particular implant(s) used. Further discussion related to suitable dosing regimens for trenbolone acetate may be found in, for example, U.S. Pat. Nos. 4,900,735 and 6,498,153 (now U.S. Pat. No. RE 39,592 E). Both those patents are incorporated by reference into this patent.

In some embodiments, the combination of this invention also (or alternatively) may be administered as part of a dosing scheme with zeranol, estradiol, and/or estradiol benzoate. It is contemplated that the zeranol, estradiol, or estradiol benzoate may be administered orally in the feed. Typically, however, zeranol, estradiol, or estradiol benzoate is administered parenterally, such as via injection or a subcutaneous implant. This is particularly true for livestock. Suitable locations for a subcutaneous implant generally include, for example, behind the ear. Zeranol is marketed under the trade name Ralgro® by Schering-Plough Corporation. In some embodiments, the implant contains other active ingredients in addition to the zeranol, estradiol, or estradiol benzoate, such as, for example, trenbolone acetate. In some embodiments, the implant is implanted for from about 20 days to about 8 months before harvest, from about 20 days to about 4 months, or from about 1 to about 3 months before harvest. In some embodiments, the implant is implanted at least 40 days before harvest. The total zeranol implant dosage is typically less than about 1500 mg.

In some embodiments, the total zeranol implant dosage is from about 10 to about 150 mg. In some such embodiments, the total zeranol implant dosage is from about 30 to about 140 mg. These embodiments may be particularly useful when the recipient animal is a bovine animal. In other embodiments, the total zeranol implant dosage is from about 10 to about 50. These embodiments may be particularly useful for smaller animal recipients, such as a sheep or recently-weaned calf. The typical implant dosage for estradiol or estradiol benzoate is typically less than about 400 mg. In some embodiments, the implant dosage for estradiol or estradiol benzoate is from about 0.05 to about 50 mg. In some embodiments, implants are implanted sequentially to administer the desirable amount of zeranol, estradiol, or estradiol benzoate over time. In some embodiments, immediate- and delayed-release implant units (e.g., pellets) are implanted at the same time to administer a desirable amount of zeranol, estradiol, or estradiol benzoate over time. The timing of the implant and any subsequent implants, as well as the amount of zeranol, estradiol, or estradiol benzoate in the implant, will depend on, for example, the species of the recipient animal, the size of the recipient animal, and the formulation(s) of the particular implant(s) used. Further discussion related to suitable dosing regimens for zeranol and estradiol may be found in, for example, U.S. Pat. No. 4,900,735; and still further discussion related to suitable dosing regimens for estradiol may be found in, for example, U.S. Pat. No. 6,498,153 (now U.S. Pat. No. RE 39,592 E).

The combination of this invention also (or alternatively) may be administered as part of a dosing scheme with one or more ionophores. Suitable ionophores include, for example, monensin, lasalocid, laidlomycin propionate, bambermycin, and salts thereof. Sodium monensin, for example, is marketed under the trade name Rumensin® by Elanco Animal Health, and reportedly effective for use in cattle fed in confinement for harvest to prevent and control of coccidiosis due to *Eimeria bovis* and *Eimeria zuernii*. When administered properly, ionophores can, for example, be effective for improving feed utilization efficiency and/or increasing the rate of weight gain. The typical daily dosage for an ionophore will vary, depending on the particular ionophore, route of administration, species of the animal recipient, size of the animal recipient, etc. When, for example, the ionophore is monensin sodium and is administered in feed for cattle, a suitable daily dose is typically less than about 5000 mg/animal. In some such embodiments, for example, the daily dose is from about 10 to about 500 mg/animal, from about 50 to about 480 mg/animal, from about 50 to about 360 mg/animal, or from about 60 to about 350 mg/animal. In other embodiments, the daily dose is less than about 4.2 mg/lb body weight (9.2 mg/kg body weight). In some such embodiments, the daily dose is from about 0.14 to about 0.42 mg/lb body weight (0.31 to about 0.92 mg/kg body weight). Illustrating further, when the ionophore is lasalocid sodium and is administered in feed for cattle, a suitable daily dose is again typically less than about 4000 mg/animal. In some such embodiments, for example, the daily dose is from about 10 to about 400 mg/animal, or from about 100 to about 360 mg/animal.

The combination of this invention also (or alternatively) may be administered as part of a dosing scheme with one or more antibiotics. Suitable antibiotics include, for example, macrolide antibiotics, such as tylosin and salts thereof. Tylosin phosphate and tylosin tartrate, for example, are marketed under the trade name Tylan® by Elanco Animal Health. When administered properly, antibiotics can, for example, be effective for increasing the rate of weight gain, improving feed efficiency, and/or reducing the time for carcass trimming. It is believed that these effects stem, at least in part, from a reduction of opportunistic bacteria (e.g., *Fusobacterium necrophorum* and *Actinomyces pyogenes*) that can infect the liver. The typical daily dosage for an antibiotic will vary, depending on the antibiotic, route of administration, species of the animal recipient, size of the animal recipient, etc. When, for example, the antibiotic is tylosin phosphate and is administered in feed for cattle, a suitable daily dose is typically less than about 900 mg. In some such embodiments, the daily dose is from about 10 to about 150 mg/animal, from about 50 to about 150 mg/animal, or from about 60 to about 90 mg/animal.

This invention also is directed to kits that are, for example, suitable for use in performing the treatment methods described above.

In some embodiments, the kit comprises a zilpaterol dosage form comprising zilpaterol (or a salt thereof, such as zilpaterol hydrochloride). In some such embodiments, the kit also comprises, for example, at least one of the following: (a) a melengestrol acetate dosage form comprising melengestrol acetate, (b) instructions for administering zilpaterol (or a salt thereof) and melengestrol acetate to the animal, and (c) instructions for mixing at least a portion of the zilpaterol dosage form with melengestrol acetate. The zilpaterol dosage form may additionally comprise one or more additional components, such as, for example, one or more carrier materials and/or other active ingredients.

In some embodiments, the kit comprises a melengestrol acetate dosage form comprising melengestrol acetate. In some such embodiments, the kit also comprises, for example, at least one of the following: (a) a zilpaterol dosage form comprising zilpaterol (or a salt thereof), (b) instructions for administering melengestrol acetate and zilpaterol (or a salt thereof) to the animal, and (c) instructions for mixing at least a portion of the melengestrol acetate dosage form with zilpaterol (or a salt thereof). The melengestrol acetate dosage form may additionally comprise one or more additional components, such as, for example, one or more carrier materials and/or other active ingredients.

In some embodiments, the kits of this invention comprise instructions for orally administering at least a portion (or all) of the zilpaterol (or salt thereof) and/or melengestrol acetate to the intended recipient animal. In some such embodiments, at least a portion (or all) of the zilpaterol (or salt thereof) and melengestrol acetate are in the same dosage form. In other embodiments, the zilpaterol (or salt thereof) and melengestrol acetate are in separate dosage forms.

In some embodiments, the kits comprise other components, such as, for example, an apparatus (e.g., a syringe) to administer one or more active ingredients, and/or an apparatus to combine one or more active ingredients and/or carrier materials with one or more other active ingredients and/or carrier materials.

EXAMPLE

This example is merely illustrative, and not intended to be limiting to the remainder of this disclosure in any way.

Angus heifers and Angus cross-brad steers with a starting weight of from 686 lb (311 kg) to 934 lb (424 kg) per animal were randomized to the following treatment groups, as shown in Table 1:

1) Non-medicated, negative control (steers and heifers)
2) Zilmax®, Rumensin®, and Tylan® (steers and heifers). The Type C feed was formulated to contain 6.8 g/ton (7.5 mg/kg) zilpaterol hydrochloride, 40 g/ton (44 mg/kg) monensin sodium, and 10 g/ton (11 mg/kg) tylosin phosphate on a 90% dry mass basis ("DMB").
3) Zilmax®, Rumensin®, Tylan®, and MGA® (heifers only). The Type C feed was formulated to contain 6.8 g/ton (7.5 mg/kg) zilpaterol hydrochloride, 40 g/ton (44 mg/kg) monensin sodium, 10 g/ton (11 mg/kg) tylosin phosphate on a 90% DMB; and melengestrol acetate at a level to deliver 0.50 mg melengestrol acetate in 22.5 lb (10.2 kg) of Type C feed.

TABLE 1

Treatment Groups

| Treatment groups | Treatment period (days zero thru 14) | Withdrawal period (days 15 thru 17) |
|---|---|---|
| 1 (2 steers and 2 heifers) | Non-medicated Type C feed | Non-medicated Type C feed |
| 2 (4 steers and 4 heifers) | Type C feed containing Zilmax ®, Rumensin ®, & Tylan ® | Type C feed containing Rumensin ® & Tylan ® |
| 3 (8 heifers) | Type C feed containing Zilmax ®, Rumensin ®, Tylan ®, & MGA ® | Type C feed containing Rumensin ®, Tylan ®, & MGA ® |

The four test articles were administered orally in complete, pelleted Type C feeds with the composition shown in Table 2:

TABLE 2

Type C Feed Composition

| Ingredient name | Percent As-Fed Basis |
|---|---|
| Corn (ground) (Bulk) | 68.25 |
| Cobs Ground ¼ (Bed-O-Cobs) | 10.44 |
| Soybean Meal 48% (Bulk) | 4.97 |
| PM 42 Kane Lass (50#) | 4.70 |
| Ground Steam Rolled Oat Groats (50#) | 4.40 |
| Dehy Alfalfa 17% Meal (bulk) | 2.20 |
| Beef finisher base (50#) | 2.00 |
| Fat liquid (Bulk) | 2.00 |
| Calcium Carbonate 38% Ca (bulk) | 0.48 |
| Dical 18.5% P (bulk) | 0.31 |
| Urea (50#) | 0.25 |
| Total | 100.00 |

For the treatment groups (i.e., Groups 2 and 3), the active ingredients were mixed with the Type C feed. The non-medicated and medicated feeds were prepared at a commercial feed manufacturing facility using typical feed manufacturing procedures. The feeds were formulated to meet or exceed 1996 NRC recommendations for finishing beef cattle.

A. Body Weight Gain

As shown in Table 3 below, the average daily weight gains of the study animals increased by 9%, 92%, and 202% in Treatment Groups 1 (non-medicated), 2 (Zilmax®, Rumensin®, and Tylan®), and 3 (Zilmax®, Rumensin®, Tylan®, and MGA®), respectively, during the treatment period compared to gains observed in the pre-treatment, non-medicated feeding period.

TABLE 3

Individual Weight Gains

| Treatment group | Sex | Pre-treatment (non-medicated) average daily gain (per head) | Treatment (medicated) average daily gain (per head) | Change in average daily gain with medicated feeding* |
|---|---|---|---|---|
| 1 | Steer | 3.03 lb (1.38 kg) | 4.67 lb (2.12 kg) | 54% |
| 1 | Steer | 2.76 lb (1.25 kg) | 1.14 lb (0.52 kg) | −59% |
| 1 | Heifer | 1.90 lb (0.86 kg) | 1.19 lb (0.54 kg) | −37% |
| 1 | Heifer | 1.12 lb (0.51 kg) | 2.62 lb (1.19 kg) | 134% |
| 2 | Steer | 2.83 lb (1.28 kg) | 5.10 lb (2.32 kg) | 80% |
| 2 | Steer | 2.62 lb (1.19 kg) | 5.14 lb (2.33 kg) | 96% |
| 2 | Steer | 2.21 lb (1.00 kg) | 4.38 lb (1.99 kg) | 99% |
| 2 | Steer | 3.10 lb (1.41 kg) | 4.90 lb (2.22 kg) | 58% |
| 2 | Heifer | 2.16 lb (0.98 kg) | 3.33 lb (1.51 kg) | 55% |
| 2 | Heifer | 1.81 lb (0.82 kg) | 3.33 lb (1.51 kg) | 84% |
| 2 | Heifer | 1.57 lb (0.71 kg) | 5.00 lb (2.27 kg) | 219% |
| 2 | Heifer | 1.21 lb (0.55 kg) | 2.38 lb (1.08 kg) | 97% |
| 3 | Heifer | 1.60 lb (0.73 kg) | 3.57 lb (1.62 kg) | 123% |
| 3 | Heifer | 1.64 lb (0.74 kg) | 2.62 lb (1.19 kg) | 60% |
| 3 | Heifer | 1.21 lb (0.55 kg) | 4.05 lb (1.84 kg) | 235% |
| 3 | Heifer | 2.16 lb (0.98 kg) | 5.00 lb (2.27 kg) | 132% |
| 3 | Heifer | 1.38 lb (0.63 kg) | 4.76 lb (2.16 kg) | 245% |
| 3 | Heifer | 0.90 lb (0.41 kg) | 5.48 lb (2.49 kg) | 511% |
| 3 | Heifer | 1.03 lb (0.47 kg) | 4.29 lb (1.95 kg) | 314% |
| 3 | Heifer | 1.03 lb (0.47 kg) | 3.33 lb (1.51 kg) | 222% |

*Change in average daily weight gain in treatment (medicated) period compared to pre-treatment (non/medicated) period.

B. Type C Feed Consumption

Average daily non-medicated consumption during the 7 days preceding the initiation of medicated feeding was calculated by pen (See Table 4). During this period, the heifers and steers were offered 22.5 lb (10.2 kg) and 25.0 lb (11.4 kg), respectively, of as-fed feed per animal daily. Based on an average dry matter content of 89.08% for the non-medicated feed offered during this period, these amounts are equivalent to 22.27 lb (10.11 kg) and 24.74 lb (11.23 kg), respectively, of 90% DMB from feed offered. By subtracting unconsumed feed corrected to a 90% DMB from feed offered, the respective average daily feed consumption of the heifers and steers during this 7-day period was 21.47 lb (9.75 kg) and 20.52 lb (9.32 kg), respectively, of 90% dry matter feed per animal daily.

TABLE 4

Non-Medicated Feed Consumption for 7 Days Before Medicated Feeding Calculated on 90% Dry Matter Basis

| Day | Heifers, 4 head/pen | | | | | Steers, 5 head/pen | |
|---|---|---|---|---|---|---|---|
| | Pen 2 | Pen 3 | Pen 4 | Pen 5 | Pen 6 | Pen 8 | Pen 9 |
| | Total of 90% Dry Matter Feed Consumed | | | | | | |
| 1 | 85.1 lb (38.6 kg) | 85.1 lb (38.6 kg) | 85.1 lb (38.6 kg) | 85.1 lb (38.6 kg) | 80.2 lb (36.4 kg) | 118.8 lb (53.9 kg) | 85.5 lb (38.8 kg) |
| 2 | 85.1 lb (38.6 kg) | 85.1 lb (38.6 kg) | 85.1 lb (38.6 kg) | 85.1 lb (38.6 kg) | 80.2 lb (36.4 kg) | 118.8 lb (53.9 kg) | 97.9 lb (44.4 kg) |
| 3 | 87.1 lb (39.5 kg) | 87.1 lb (39.5 kg) | 87.1 lb (39.5 kg) | 87.1 lb (39.5 kg) | 82.2 lb (37.3 kg) | 94.4 lb (42.8 kg) | 98.3 lb (44.6 kg) |
| 4 | 87.1 lb (39.5 kg) | 87.1 lb (39.5 kg) | 87.1 lb (39.5 kg) | 87.1 lb (39.5 kg) | 82.2 lb (37.3 kg) | 107.2 lb (48.7 kg) | 95.7 lb (43.4 kg) |
| 5 | 89.1 lb (40.4 kg) | 89.1 lb (40.4 kg) | 89.1 lb (40.4 kg) | 89.1 lb (40.4 kg) | 84.1 lb (38.2 kg) | 121.2 lb (55.0 kg) | 59.9 lb (27.2 kg) |
| 6 | 89.1 lb (40.4 kg) | 89.1 lb (40.4 kg) | 89.1 lb (40.4 kg) | 89.1 lb (40.4 kg) | 86.1 lb (39.1 kg) | 121.2 lb (55.0 kg) | 106.6 lb (48.4 kg) |
| 7 | 86.0 lb (39.0 kg) | 89.1 lb (40.4 kg) | 84.6 lb (38.4 kg) | 78.3 lb (35.5 kg) | 82.1 lb (37.3 kg) | 119.1 lb (54.1 kg) | 91.4 lb (41.5 kg) |
| Total feed consumed in 7 days | 608.6 lb (276.3 kg) | 611.7 lb (277.7 kg) | 607.2 lb (275.7 kg) | 600.9 lb (272.8 kg) | 576.9 lb (261.9 kg) | 800.8 lb (363.6 kg) | 635.3 lb (288.4 kg) |
| 7-day average of daily 90% DMB feed consumed (per head) by pen | 21.74 lb (9.87 kg) | 21.85 lb (9.92 kg) | 21.69 lb (9.85 kg) | 21.46 lb (9.74 kg) | 20.61 lb (9.36 kg) | 22.88 lb (10.39 kg) | 18.15 lb (8.24 kg) |

Average daily feed consumption by treatment group, pen, and sex also was calculated for the Zilmax® treatment (15 days) and withdrawal (3 days) periods of the study. The results are shown in Table 5 and 6. During these periods, the heifers and steers were again offered 22.5 lb (10.2 kg) and 25.0 lb (11.4 kg), respectively, of as-fed feed per animal each day. By using the average dry matter percent of the Type C feeds offered during these periods, the amount of feed offered on a 90% DMB was calculated. Unconsumed feed corrected to a 90% DMB was then subtracted from feed offered to calculate average daily feed consumption on a 90% DMB. Consumptions for treatment groups 1, 2, and 3 during the combined Zilmax® treatment period and withdrawal periods were 22.92 lb (10.40 kg), 21.24 lb (9.64 kg), and 21.35 lb (9.69 kg), respectively, of feed (90% DMB) per animal daily.

TABLE 5

Daily Feed Consumption During the Zilmax® Treatment Period (15 days) and Withdrawal Period (3 days) Calculated on a 90% Dry Matter Basis

| Day | Steers (2 head) Pen 2 Non-medicated control | Heifers (2 head) Pen 3 Non-medicated control | Steers (4 head) Pen 5 Zilmax®, Rumensin®, & Tylan® | Heifers (4 head) Pen 6 Zilmax®, Rumensin®, & Tylan® | Heifers (4 head) Pen 8 Zilmax®, Rumensin®, Tylan®, & MGA® | Heifers (4 head) Pen 9 Zilmax®, Rumensin®, Tylan®, & MGA® |
|---|---|---|---|---|---|---|
| | | | Total 90% Dry Matter Feed Consumed | | | |
| 1 | 48.1 lb (21.8 kg) | 44.5 lb (20.2 kg) | 94.9 lb (43.1 kg) | 89.0 lb (40.4 kg) | 87.7 lb (39.8 kg) | 89.1 lb (40.4 kg) |
| 2 | 48.7 lb (22.1 kg) | 44.5 lb (20.2 kg) | 78.2 lb (35.5 kg) | 89.5 lb (40.6 kg) | 61.9 lb (28.1 kg) | 89.1 lb (40.4 kg) |
| 3 | 48.4 lb (22.0 kg) | 44.5 lb (20.2 kg) | 90.1 lb (40.9 kg) | 89.5 lb (40.6 kg) | 69.9 lb (31.7 kg) | 88.2 lb (40.0 kg) |
| 4 | 42.9 lb (19.5 kg) | 44.5 lb (20.2 kg) | 87.1 lb (39.5 kg) | 88.7 lb (40.3 kg) | 76.6 lb (34.8 kg) | 86.0 lb (39.0 kg) |
| 5 | 45.4 lb (20.6 kg) | 43.9 lb (19.9 kg) | 87.9 lb (39.9 kg) | 84.8 lb (38.5 kg) | 82.2 lb (37.3 kg) | 83.2 lb (37.8 kg) |
| 6 | 44.2 lb (20.1 kg) | 44.2 lb (20.1 kg) | 85.7 lb (38.9 kg) | 85.0 lb (38.6 kg) | 83.5 lb (37.9 kg) | 86.3 lb (39.2 kg) |
| 7 | 49.5 lb (22.5 kg) | 44.5 lb (20.2 kg) | 79.2 lb (36.0 kg) | 81.7 lb (37.1 kg) | 87.0 lb (39.5 kg) | 88.7 lb (40.3 kg) |
| 8 | 49.5 lb (22.5 kg) | 44.5 lb (20.2 kg) | 83.2 lb (37.8 kg) | 83.1 lb (37.7 kg) | 85.8 lb (39.0 kg) | 89.1 lb (40.4 kg) |
| 9 | 49.5 lb (22.5 kg) | 44.5 lb (20.2 kg) | 93.8 lb (42.6 kg) | 71.6 lb (32.5 kg) | 84.1 lb (38.2 kg) | 89.1 lb (40.4 kg) |
| 10 | 49.5 lb (22.5 kg) | 41.1 lb (18.6 kg) | 80.3 lb (36.4 kg) | 72.9 lb (33.1 kg) | 78.2 lb (35.5 kg) | 89.1 lb (40.4 kg) |
| 11 | 49.5 lb (22.5 kg) | 44.5 lb (20.2 kg) | 96.9 lb (44.0 kg) | 79.6 lb (36.1 kg) | 84.4 lb (38.3 kg) | 89.1 lb (40.4 kg) |
| 12 | 49.5 lb (22.5 kg) | 44.5 lb (20.2 kg) | 93.4 lb (42.4 kg) | 60.4 lb (27.4 kg) | 89.1 lb (40.4 kg) | 89.1 lb (40.4 kg) |
| 13 | 49.5 lb (22.5 kg) | 44.5 lb (20.2 kg) | 95.9 lb (43.5 kg) | 63.7 lb (28.9 kg) | 89.1 lb (40.4 kg) | 89.1 lb (40.4 kg) |
| 14 | 49.5 lb (22.5 kg) | 44.5 lb (20.2 kg) | 99.4 lb (45.1 kg) | 87.0 lb (39.5 kg) | 89.1 lb (40.4 kg) | 89.1 lb (40.4 kg) |
| 15 | 49.5 lb (22.5 kg) | 44.5 lb (20.2 kg) | 99.4 lb (45.1 kg) | 88.5 lb (40.2 kg) | 88.7 lb (40.3 kg) | 89.1 lb (40.4 kg) |
| W1 | 48.9 lb (22.2 kg) | 44.5 lb (20.2 kg) | 88.0 lb (40.0 kg) | 76.6 lb (34.8 kg) | 86.7 lb (39.4 kg) | 89.2 lb (40.5 kg) |
| W2 | 48.9 lb (22.2 kg) | 44.5 lb (20.2 kg) | 97.8 lb (44.4 kg) | 78.1 lb (35.4 kg) | 82.9 lb (37.6 kg) | 88.4 lb (40.1 kg) |
| W3 | 35.3 lb (16.0 kg) | 41.4 lb (18.8 kg) | 81.5 lb (37.0 kg) | 76.2 lb (34.6 kg) | 78.4 lb (35.6 kg) | 88.2 lb (40.0 kg) |

TABLE 6

Summary of Total Feed Consumption and Average Daily Feed Consumption During the Zilmax® Treatment Period and Withdrawal Period on a 90% DMB

| | Steers (2 head) Pen 2 Non-medicated control | Heifers (2 head) Pen 3 Non-medicated control | Steers (4 head) Pen 5 Zilmax®, Rumensin®, & Tylan® | Heifers (4 head) Pen 6 Zilmax®, Rumensin®, & Tylan® | Heifers (4 head) Pen 8 Zilmax®, Rumensin®, Tylan®, & MGA® | Heifers (4 head) Pen 9 Zilmax®, Rumensin®, Tylan®, & MGA® |
|---|---|---|---|---|---|---|
| Total feed consumed in treatment period | 723.2 lb (328.3 kg) | 663.7 lb (301.3 kg) | 1345.4 lb (610.8 kg) | 1215.1 lb (551.6 kg) | 1237.3 lb (561.7 kg) | 1323.4 lb (600.8 kg) |

TABLE 6-continued

Summary of Total Feed Consumption and Average Daily Feed Consumption
During the Zilmax ® Treatment Period and Withdrawal Period on a 90% DMB

|  | Steers (2 head) Pen 2 Non-medicated control | Heifers (2 head) Pen 3 Non-medicated control | Steers (4 head) Pen 5 Zilmax ®, Rumensin ®, & Tylan ® | Heifers (4 head) Pen 6 Zilmax ®, Rumensin ®, & Tylan ® | Heifers (4 head) Pen 8 Zilmax ®, Rumensin ®, Tylan ®, & MGA ® | Heifers (4 head) Pen 9 Zilmax ®, Rumensin ®, Tylan ®, & MGA ® |
|---|---|---|---|---|---|---|
| Total feed consumed in Withdrawal period | 133.1 lb (60.4 kg) | 130.4 lb (59.2 kg) | 267.3 lb (121.4 kg) | 230.9 lb (104.8 kg) | 248.1 lb (112.6 kg) | 265.8 lb (120.7 kg) |
| Total consumed (all 18 days) | 856.3 lb (388.8 kg) | 794.1 lb (360.5 kg) | 1612.8 lb (732.2 kg) | 1446.0 lb (656.5 kg) | 1485.4 lb (674.4 kg) | 1589.3 lb (721.5 kg) |
| Average daily feed consumed in treatment period (per head) by pen | 24.11 lb (10.94 kg) | 22.12 lb (10.04 kg) | 22.42 lb (10.18 kg) | 20.25 lb (9.19 kg) | 20.62 lb (9.36 kg) | 22.06 lb (10.02 kg) |
| Average Daily feed consumed in withdrawal period (per head) by pen | 22.19 lb (10.07 kg) | 21.74 lb (9.87 kg) | 22.28 lb (10.11 kg) | 19.24 lb (8.73 kg) | 20.67 lb (9.38 kg) | 22.15 lb (10.06 kg) |
| Total average daily feed consumed (per head) by pen (all 18 days) | 23.79 lb (10.80 kg) | 22.06 lb (10.02 kg) | 22.40 lb (10.17 kg) | 20.08 lb (9.12 kg) | 20.63 lb (9.37 kg) | 22.07 lb (10.02 kg) |

The words "comprise", "comprises", and "comprising" in this patent (including the claims) are to be interpreted inclusively rather than exclusively. This interpretation is intended to be the same as the interpretation that these words are given under United States patent law.

The term "pharmaceutically acceptable" is used adjectivally to mean that the modified noun is appropriate for use in a pharmaceutical product. When it is used, for example, to describe a salt or carrier material, it characterizes the salt or carrier material as not being deleterious to the intended recipient animal to the extent that the deleterious effect(s) outweighs the benefit(s) of the salt or carrier material.

This patent sometimes refers to concentrations of various ingredients in an animal feed based on the feed containing approximately 90% dry matter. This stems from the fact that the dry matter content in many typical animal feeds is approximately 90%. This is particularly true for livestock feeds, such as feeds for bovine animals. It should be recognized that such concentrations can be adjusted to account for other dry matter percentages in a feed. To illustrate, if a desired concentration of an ingredient is described as a specific concentration based on the feed having 90% dry matter, the desired concentration in a feed containing no water would be the specific concentration divided by 0.9.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method for improving feed utilization efficiency or increasing the rate of weight gain in an animal, wherein the method comprises administering to the animal an effective amount of zilpaterol (or a salt thereof), an effective amount of melengestrol acetate, an effective amount of monensin (or a salt thereof) and an effective amount of tylosin (or a salt thereof).

2. The method of claim 1, wherein the amount of the zilpaterol (or salt thereof) and the amount of melengestrol acetate are, when combined, sufficient to improve the animal's average daily feed utilization efficiency over a period of at least about 3 days relative to the average daily feed utilization efficiency that would be realized by administering the amount of the zilpaterol (or salt thereof) without any melengestrol acetate over the same amount of time under otherwise substantially identical feeding conditions.

3. The method of claim 2, wherein the amount of the zilpaterol (or salt thereof) and the amount of melengestrol acetate are, when combined, sufficient to increase the animal's average daily weight gain over a period of at least about 3 days by at least about 100% the average daily weight gain that is realized during the week immediately before administration of the zilpaterol (or salt thereof) and melengestrol acetate under otherwise substantially identical feeding conditions.

4. The method of claim 1, wherein the amount of the zilpaterol (or salt thereof) and the amount of melengestrol acetate are, when combined, sufficient to increase the animal's average daily weight gain over a period of at least about 3 days relative to the average daily weight gain that would be realized by administering the amount of the zilpaterol (or salt thereof) without any melengestrol acetate over the same amount of time under otherwise substantially identical feeding conditions.

5. The method of claim 4, wherein the amount of the zilpaterol (or salt thereof) and the amount of melengestrol acetate are, when combined, sufficient to increase the animal's average daily weight gain over a period of at least about 3 days by at least about 1.2 times the average daily weight gain that would be realized by administering the amount of the zilpaterol (or salt thereof) without any melengestrol acetate over the same amount of time under otherwise substantially identical feeding conditions.

6. The method of claim 1, wherein at least a portion of the zilpaterol (or salt thereof) and at least a portion of the melengestrol acetate are administered in a single formulation.

7. The method of claim 1, wherein at least a portion of the zilpaterol (or salt thereof) is administered in a separate formulation from at least a portion of the melengestrol acetate.

8. The method of claim 1, wherein at least a portion of the zilpaterol (or salt thereof) or at least a portion of the melengestrol acetate is administered orally.

9. The method of claim 1, wherein the zilpaterol (or salt thereof) and the melengestrol acetate are administered orally.

10. The method of claim 1, wherein the method comprises administering zilpaterol hydrochloride.

11. The method of claim 1, wherein the method further comprises administering at least one additional steroid.

12. The method of claim 1, wherein the method further comprises administering trenbolone acetate.

13. The method of claim 1, wherein the method further comprises administering zeranol, estradiol, or estradiol benzoate.

14. The method of claim 1, wherein the method further comprises administering at least one ionophore.

15. The method of claim 1, wherein the method comprises administering monensin sodium.

16. The method of claim 1, wherein the method further comprises administering at least one antibiotic.

17. The method of claim 1, wherein the method comprises administering tylosin phosphate or tylosin tartrate.

18. The method of claim 1, wherein the animal is a bovine animal.

19. The method of claim 1, wherein the animal is a swine animal.

20. The method of claim 1, wherein the animal is a bird.

21. The method of claim 1, wherein the animal is a fish.

* * * * *